United States Patent

Showell

[11] 4,353,906
[45] Oct. 12, 1982

[54] CHROMANOL DERIVATIVES AND THEIR USE FOR TREATING HYPERTENSION

[75] Inventor: Graham A. Showell, Harlow, England

[73] Assignee: Beecham Group Limited, England

[21] Appl. No.: 230,540

[22] Filed: Feb. 2, 1981

[30] Foreign Application Priority Data

Feb. 2, 1980 [GB] United Kingdom ............... 8003594

[51] Int. Cl.³ .................. A61K 31/505; C07D 487/04
[52] U.S. Cl. .................................... 424/251; 544/250; 549/412; 549/401; 549/404; 549/408; 549/387
[58] Field of Search .................. 544/250; 424/251

[56] References Cited

U.S. PATENT DOCUMENTS

| | | | |
|---|---|---|---|
| 2,530,025 | 11/1950 | Moergelim et al. | 544/246 X |
| 3,963,717 | 6/1976 | Cooke et al. | 424/251 X |
| 4,199,584 | 4/1980 | Cox et al. | 424/251 |
| 4,272,535 | 6/1981 | Blythin | 424/251 X |

Primary Examiner—Donald G. Daus
Assistant Examiner—Diana G. Rivers
Attorney, Agent, or Firm—Jacobs & Jacobs

[57] ABSTRACT

Compounds of the formula (I):

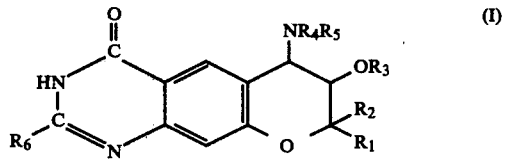

wherein:
$R_1$ and $R_2$ are independently selected from a hydrogen atom and a $C_{1-3}$ alkyl group;
$R_3$ is a hydrogen atom, a $C_{1-3}$ alkyl or $C_{2-4}$ acyl group;
$R_4$ is a hydrogen atom or $C_{1-5}$ alkyl group;
$R_5$ is a $C_{1-5}$ alkyl group, a straight chain $C_{1-3}$ alkyl group terminally substituted by a chlorine atom; or
$R_4$ and $R_5$ are joined so that together with the nitrogen atom to which they are attached they form a 5-, 6- or 7-membered ring optionally containing an oxygen or sulphur atom;
$R_6$ is a $C_{1-5}$ alkyl group;
the $NR_4R_5$ and $OR_3$ moieties are trans; and pharmaceutically acceptable salts thereof having antihypertensive activity, processes for their preparation and their use in compositions.

8 Claims, No Drawings

CHROMANOL DERIVATIVES AND THEIR USE FOR TREATING HYPERTENSION

This invention relates to novel compounds having blood pressure lowering activity, to a process for their preparation, and to pharmaceutical compositions containing them.

U.K. Pat. Nos. 1,495,526 and 1,511,187 disclose that derivatives of trans-3-hydroxy-4-aminochroman have blood pressure lowering activity.

A structurally distinct group of compounds have now been found that also possess good blood pressure lowering activity with fewer unwanted cardiac effects.

Accordingly, the present invention provides a compound of the formula (I):

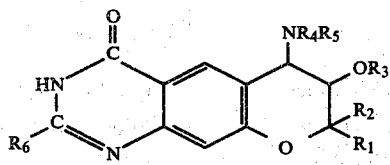

wherein:
$R_1$ and $R_2$ are independently selected from a hydrogen atom and a $C_{1-3}$ alkyl group;
$R_3$ is a hydrogen atom, a $C_{1-3}$ alkyl or $C_{2-4}$ acyl group;
$R_4$ is a hydrogen atom or $C_{1-5}$ alkyl group;
$R_5$ is a $C_{1-5}$ alkyl group, a straight chain $C_{1-3}$ alkyl group terminally substituted by a chlorine atom; or
$R_4$ and $R_5$ are joined so that together with the nitrogen atom to which they are attached they form a 5-, 6- or 7-membered ring optionally containing an oxygen or sulphur atom;
$R_6$ is a $C_{1-5}$ alkyl group;
the $NR_4R_5$ and $OR_3$ moieties are trans; and pharmaceutically acceptable salts thereof.

Suitably $R_1$ is a hydrogen atom or a methyl or ethyl group. Most suitably $R_1$ is a methyl group. Suitably $R_2$ is a hydrogen atom or a methyl or ethyl group. Most suitably $R_2$ is a methyl group.

Apt values for $R_3$ include the hydrogen atom, the methyl and ethyl groups, and the acetyl group. Particularly apt values for $R_3$ include the hydrogen atom and the methyl group. A favoured value for $R_3$ is the hydrogen atom.

Suitable acyclic values of the $NR_4R_5$ moiety include those wherein $R_4$ is a hydrogen atom or methyl group and $R_5$ is an alkyl group. Specific values for acyclic $NR_4R_5$ moieties include dimethylamino, isopropylamino and t-butylamino.

Suitable cyclic values for the $NR_4R_5$ moiety include those of the sub-formula (a):

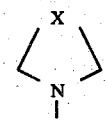

wherein X is a bond, a methylene group, an ethylene group, an ethylidene group, an oxygen or a sulphur atom. Most suitably X is a bond or a methylene group.

Suitable examples of $R_6$ include the methyl, ethyl and n- and iso-propyl groups. Preferably $R_6$ is methyl.

Suitable salts of the compounds of this invention include acid addition salts with pharmaceutically acceptable inorganic or organic acids such as hydrochloric, hydrobromic, phosphoric, sulphuric, toluene sulphonic, methane sulphonic, acetic propionic, succinic, citric, lactic, tartaric, maleic, mandelic or the like.

From the aforesaid it will be appreciated that a preferred group of compounds within formula (I) is of formula (II):

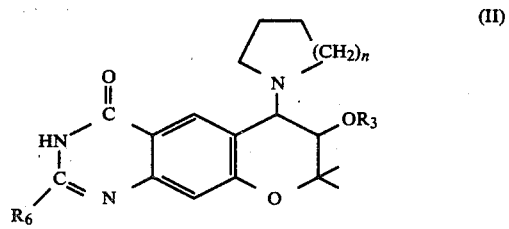

wherein n is 1 or 2, $R_3$ and $R_6$ are as hereinbefore defined, and the cyclic amino and $OR_3$ moieties are trans.

Preferably n is 1.

Suitable and preferred examples of $R_3$ and $R_6$ are as described.

Preferably in formula (II) $R_3$ is hydrogen.
Preferably in formula (II) $R_6$ is methyl.

The invention also provides a process for the preparation of compounds of the formula (I), which process comprises cyclising a compound of formula (III):

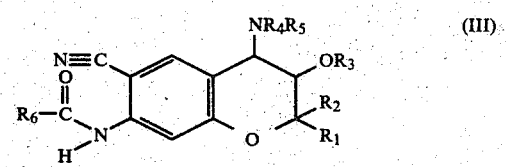

wherein the variable groups are hereinbefore described.

The cyclisation reaction may suitably be carried out with aid. For example a solution of the compound of formula (III) in an organic solvent, such as ethyl acetate, is treated with an acid, such as hydrochloric acid, followed by basification and phase separation. The desired compound of formula (I) is then isolated from the organic phase by, for example, evaporation.

Thereafter if desired a thus formed compound of the formula (I) wherein $R_3$ is hydrogen may be alkylated or acylated in conventional manner to give the corresponding compounds wherein $R_3$ is alkyl and acyl; and salts may be formed.

The compounds of the invention exist in optically active forms. Those skilled in the chemical arts will realise that racemic mixtures of amino compounds can be separated into pure optical isomers using such techniques as fractional crystallisation using optically active acids or the like. All such forms, and mixtures thereof, are covered by this invention.

Compounds of the formula (III) may be prepared by the reaction of a compound of the formula (IV):

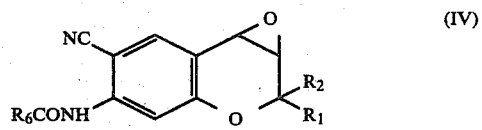

wherein $R_1$, $R_2$ and $R_6$ are as defined in relation to formula (I), with a compound of formula (V):

HNR₄R₅ (V)

wherein $R_4$ and $R_5$ are as defined in relation to formula (I).

The reaction of the epoxide may be carried out at any non-extreme low, medium or high temperature (for example, −10° to 200° C.) but in general ambient or slightly elevated temperatures are most suitable (for example 12° to 100° C.). The reaction is normally carried out in a solvent such as a lower alcohol or lower ketone, for example methanol, ethanol, propanol, acetone or methylethylketone.

It has been found that the reaction proceeds smoothly if carried out in refluxing ethanol.

Alternatively, if a high boiling amine of formula (V) is used (for example pyrrolidine or piperidine) compounds of the formula (II) may be prepared by reaction of the bromohydrin of formula (VI)

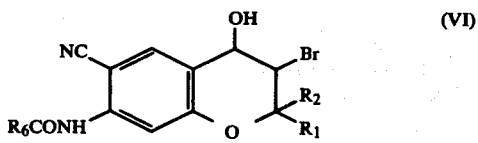

(VI)

with the amine of formula (V) in a solvent such as lower alcohol, for example ethanol, or by using the amine itself as solvent.

The above reaction gives a trans product substantially free of the cis-isomer.

The desired product may be obtained from the reaction mixture by removal of the solvent which is normally accomplished by evaporation under reduced pressure. The initial product may contain some epoxide. This may be separated by dissolving the reaction product in ethyl acetate and extracting into dilute acid. If desired the solvent may be evaporated at this stage but it is usually more convenient to neutralise, back extract into ethyl acetate and recover by evaporation at reduced pressure. If a salt is desired this product (the free base) may be dissolved in diethyl ether containing a little ethanol and treated with a solution of the acid for example in diethyl ether. The desired salt may then be collected by filtration.

The epoxides of the formula (IV) maybe isolated or used in situ and may be prepared according to the following reaction sequence.

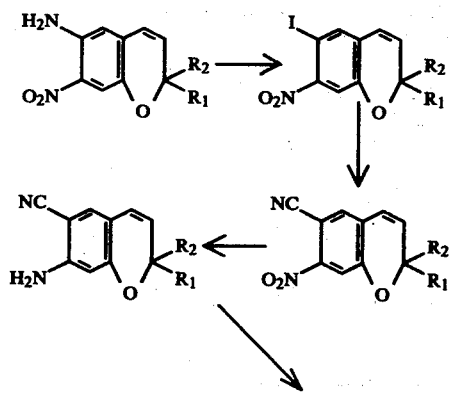

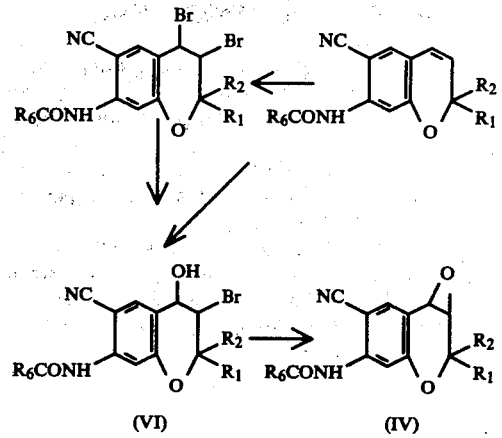

(VI)          (IV)

This reaction sequence may be brought about under conditions as described in the aforementioned British Patents.

In a further aspect the present invention also provides a pharmaceutical composition which comprises a compound of this invention and a pharmaceutically acceptable carrier.

The compositions of this invention are most suitably adapted for oral administration although adaption for other modes of administration for example by injection, are also possible.

In order to obtain consistency of administration, it is preferred that the compositions of this invention are in the form of a unit-dose. Suitable unit dose forms include tablets, capsules, ampoules and powders in sachets. Such unit dose forms aptly contain from 1 to 100 mg of the compound of this invention and more usually from 2 to 15 mg, for example 5 to 50 mg. Such compositions may be administered from 1 to 6 times a day, more usually from 2 to 4 times a day, in a manner such that the daily dose is from 5 to 200 mg for a 70 kg human adult and more aptly from 10 to 100 mg.

Shaped compositions are favoured composition aspects.

The compositions of this invention may be formulated in conventional manner, for example in a manner similar to that used for known antihypertensive agents such as hydrallizine.

In addition such compositions may contain further active agents such as other anti-hypertesnive agents especially β-blocking agents, and diuretics.

The invention further provides a method of treatment of prophylaxis of hypertension in mammals including man which comprises the administration of an effective amount of a compound of formula (I) or a pharmaceutically acceptable salt thereof.

The following Examples illustrate the invention.

EXAMPLE 1

(a)

7-Acetamido-6-cyano-3,4-dihydro-2,2-dimethyl-trans-4-pyrrolidino-2H-benzo[b]pyran-3-ol

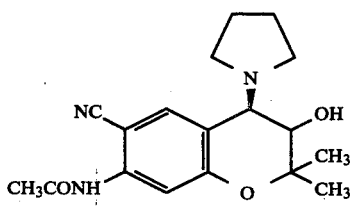

(i) 2,2-Dimethyl-6-iodo-7-nitro-2H-benzo[b]pyran

To a cooled solution of 6-amino-2,2-dimethyl-7-nitro-2H-benzo[b]pyran (20.0 g)* in glacial acetic acid (800 ml) was added concentrated sulphuric acid (400 ml) and the solution stirred at 8° C. Nitrosyl sulphuric acid (prepared by dissolving sodium nitrite (6.62 g) in cold concentrated sulphuric acid (200 ml) the mixture being warmed to dissolved the solid then re-cooled to approximately 4° C.) was added keeping the temperature of the reaction mixture below 12° C. The dark, viscous mixture was stirred at approximately 7° C. for a further hour then poured into a cold (approximately 5° C.) solution of potassium iodide (15.27 g) in water (200 ml). Toluene (800 ml) was added to dissolve the resulting precipitate and the mixture stirred in an ice bath for 20 minutes, then at room temperature for 18 hours. The reaction mixture was diluted with water (500 ml), the organic phase was separated, washed with water, dried and evaporated in vacuo to afford the required 2,2-dimethyl-6-iodo-7-nitro-2H-benzo[b]pyran (11.84 g, 39%) as a red gum.

*the preparation of this compound was disclosed in British Patent No. 1,548,222.

n.m.r. (CDCl$_3$):
δ1.43 (s, 6H);
5.79 (d, J=10, 1H);
6.25 (d, J=10, 1H);
7.28 (s, 1H);
7.51 (s, 1H).

This compound was used immediately in the next step.

(ii) 6-Cyano-2,2-dimethyl-7-nitro-2H-benzo[b]pyran

This crude benzopyran (11.74 g), cuprous cyanide (3.20 g) and anhydrous pyridine (450 ml) were heated under reflux for 8 hours. The mixture was concentrated to approximately half volume then diluted with water (1 liter) and the resulting emulsion extracted into ethyl acetate, the organic phase was washed with water, dried and evaporated in vacuo to afford a brown solid (9.62 g) which was purified on a silica gel column using ethyl acetate, 60°-80° petroleum ether mixtures by a gradient elution technique, to give 6-cyano-2,2-dimethyl-7-nitro-2H-benzo[b]pyran (4.00 g) as orange crystals. A small sample was recrystallised from ethyl acetate, 60°-80° petroleum ether to yield orange crystals, mp 154°-155° C.

n.m.r. (CDCl$_3$):
δ1.51 (s, 6H);
5.89 (d, J=10, 1H);
6.34 (d, J=10, 1H);
7.40 (s, 1H);
7.62 (s, 1H);

i.r. (nujol mull) 2220, 1530, 1330 cm$^{-1}$.

Analysed: Calculated for $C_{12}H_{10}N_2O_3$: C, 62.61; H, 4.38; N, 12.17. Found: C, 62.40; H, 4.51; N, 12.04%.

(iii) 7-Amino-6-cyano-2,2-dimethyl-2H-benzo[b]pyran

This benzopyran (2.29 g), electrolytic iron powder (1.94 g) and glacial acetic acid (100 ml) were stirred at 100° C. (oil bath temperature) for 1 hour. Dilution with water and extraction into ethyl acetate, washing of the organic phase with water, brine, drying and removal of solvent in vacuo afforded 7-amino-6-cyano-2,2-dimethyl-2H-benzo[b]pyran (1.98 g) as dark orange crystals. A small sample was recrystallised twice from ethyl acetate, 60°-80° petroleum ether to give yellow crystals, mp 137°-138° C.

n.m.r. (CDCl$_3$):
δ1.39 (s, 6H);
4.20-4.52 (broad, 2H, exch. with D$_2$O);
5.48 (d, J32 10, 1H);
6.10 (s, 1H); overlapped with
6.16 (d, J=10, 1H);
6.97 (s, 1H).

i.r. (nujol mull) 3340, 3240, 2220 cm$^{-1}$.

Analysis: Calculated for $C_{12}H_{12}N_2O$; C, 71.98; H, 6.04; N, 13.99. Found: C, 71.31; H, 5.84; N, 13.49%.

Mass spectrum: m/e=200.

(iv) 7-Acetamido-6-cyano-2,2-dimethyl-2H-benzo[b]pyran

This benzopyran (1.88 g) was stirred vigorously with acetic anhydride (30 ml) in ethanol (80 ml) at room temperature for 8 hours. The reaction mixture was evaporated in vacuo to afford 7-acetamido-6-cyano-2,2-dimethyl-2H-benzo[b]pyran as a dark orange solid (2.20 g). A small sample was recrystallised twice from ethyl acetate, 60°-80° petroleum ether to give yellow crystals, mp 136°-137° C.

n.m.r. (CDCl$_3$):
δ1.43 (s, 6H);
2.21 (s, 3H);
5.61 (d, J=10, 1H);
6.20 (d, J=10, 1H);
7.11 (s, 1H);
7.40-7.64 (broad, 1H, exch. with D$_2$O);
7.84 (s, 1H);

i.r. (chloroform solution): 3410, 2200, 1700 cm$^{-1}$.

Analysis: Calculated for $C_{14}H_{14}N_2O_2$: C, 69.41; H, 5.82; N, 11.56. Found: C, 69.20; H, 5.98; N, 11.53%.

(v)

7-Acetamido-trans-3-bromo-6-cyano-3,4-dihydro-2,2-dimethyl-2H-benzo[b]pyran-4-ol To this benzopyran (2.06 g) dissolved in dimethyl sulphoxide (50 ml) and water (0.18 ml) was added N-bromo-succinimide (1.74 g) with stirring. After 30 minutes the mixture was diluted with water, extracted into ethyl acetate, the organic phase was washed with water, brine, dried and evaporated in vacuo to give 7-acetamido-trans-3-bromo-6-cyano-3,4-dihydro-2,2-dimethyl-2H-benzo[b]pyran-4-ol as an orange solid (2.44 g). Recrystallisation from ethyl acetate, 60°-80° petroleum ether gave yellow crystals (1.62 g), mp 191°-192° C.

n.m.r. (CDCl$_3$):
1.40 (s, 3H);
1.60 (s, 3H);
2.21 (s, 3H);

2.68–2.82 (m, 1H, exch. with D₂O);
4.04 (d, J=10, 1H);
4.83 (m, falls to d with D₂O, J=10, 1H);
7.43–7.58 (m, exch. with D₂O, 1H);
7.71 (s, 1H);
7.89 (s, 1H);

i.r. (nujol mull) 3100–3500, 2225, 1685 cm⁻¹.

Analysis. Calculated for $C_{14}H_{15}BrN_2O_3$: C, 49.58; H, 4.46; N, 8.26. Found: C, 49.87; H, 4.62; N, 8.19%.

(vi)

7-Acetamido-6-cyano-3,4-dihydro-2,2-dimethyl-trans-4-pyrrolidino-2H-benzo[b]pyran-3-ol This bromohydrin (1.62 g) and pyrrolidine (0.80 ml) were refluxed in ethanol (50 ml) for 24 hours. The reaction mixture was evaporated in vacuo to afford a brown gum which was dissolved in chloroform, washed with sodium carbonate solution, water, dried and evaporated in vacuo to give a brown foam (1.51 g), which was chromatographed on a silica gel column using ethyl acetate, 60°–80° petroleum ether mixtures in a gradient elution technique to afford 7-acetamido-6-cyano-3,4-dihydro-2,2-dimethyl-trans-4-pyrrolidino-2H-benzo[b]-pyran-3-ol as a dark yellow solid (0.79 g). A sample was recrystallised from ethyl acetate, 60°–80° petroleum ether to give yellow crystals, mp 175°–176° C.

n.m.r. (CDCl₃)
δ1.22 (s, 3H);
1.50 (s, 3H);
1.72–2.04 (m, 4H);
2.22 (s, 3H);
2.57–3.14 (m, 5H);
3.58 (d, J=10, 1H);
3.95 (d, J=10, 1H);
7.43 (s) overlapped with
7.43 (broad, total of 2H);
7.79 (s, 1H);

i.r. (chloroform solution) 3410, 2200, 1700 cm⁻¹.

Analysis. Calculated for $C_{18}H_{23}N_3O_3$: C, 65.63; H, 7.04; N, 12.76. Found: C, 64.51; H, 6.87; N, 12.28%.

Consistent analysis was not obtained. Mass spectrum: Chemical Ionization, (M+H)⁺ at m/e 330.

(b)

Trans-7-hydroxy-6-pyrrolidino-4,6,7,8-tetrahydro-2,8,8-trimethyl-3H-pyrano[3,2-g]quinazolin-4-one dihydrochloride (1)

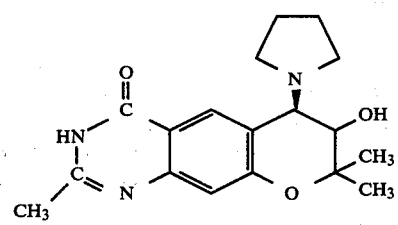

7-Acetamido-6-cyano-3,4-dihydro-2,2-dimethyl-trans-4-pyrrolidino-2H-benzo[b]pyran-3-ol (0.44 g) was stirred vigorously with 5 N hydrochloric acid (40 ml) in ethyl acetate (40 ml) for 10 minutes at room temperature. The mixture was basified with 10% sodium hydroxide solution followed by separation of the organic layer and washing with water, then brine, drying and evaporation to dryness under reduced pressure to give a light brown foam (0.43 g).

n.m.r. (DMSO d₆):
δ1.16 (s);
1.41 (s);
1.58–1.86 (m);
2.28 (s);
2.62–3.01 (m);
3.68–4.09 (m);
5.29 (d, J=5, exch. with D₂O);
6.73 (s);
8.17 (s);
11.71–11.98 (m, exch. with D₂O).

The crude free base was dissolved in ethanol and addition of ethereal-HCl precipitated the salt which was recrystallised from aqueous ethanol to give trans-7-hydroxy-6-pyrrolidino-4,6,7,8-tetrahydro-2,8,8-trimethyl-3H-pyrano[3,2-g]quinazolin-4-one dihydrochloride (0.25 g) as light brown powdery crystals.

i.r. (KBr disc): 1715, 1660 cm⁻¹.

Analysis: Calculated for $C_{18}H_{23}N_3O_3 \cdot 2HCl$: C, 53.74; H, 6.26; N, 10.44. Found: C, 54.14; H, 6.64; N, 10.17%. Mp 258°–260° C. Mass spectrum: chemical ionization, m/e=330 for [M+H−2HCl]⁺.

DEMONSTRATION OF EFFECTIVENESS

Biological Data

Systolic blood pressures were recorded by a modification of the tail cuff method described by J. M. Claxton, M. G. Palfreyman, R. H. Poyser and R. L. Whiting, European Journal of Pharmacology, 37, 179 (1976). An oscilloscope o W+W BP recorder, model 8002, was used to display pulses. Prior to all measurements rats were placed in a heated environment (33.5°±0.5° C.) before transfer to a restraining cage. Each determination of blood pressure was the mean of at least 6 readings. Spontaneously hypertensive rats (aged 12–18 weeks) with systolic blood pressures >170 mmHg were considered hypertensive.

| Compound of Example No. | Time Post Dose (hrs) | % Change in Systolic Blood Pressure | % Change in Heart Rate |
|---|---|---|---|
| | Initial Value | 198 ± 2 | 439 ± 20 |
| (1b) at 1 mg/kg p.o. using 6 rats | 1 | −15 ± 3 | +1 ± 4 |
| | 2 | −18 ± 2 | +7 ± 7 |
| | 4 | −26 ± 2 | +5 ± 7 |
| | 6* | −35 | +11 |

*At 6 hrs only 4 rats had measurable pulses.

Toxicity

No toxic effects were observed during these tests.

We claim:

1. A compound of the formula (I):

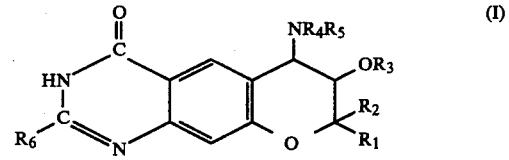

wherein:

$R_1$ and $R_2$ are independently selected form a hydrogen atom and a $C_{1-3}$ alkyl group;

$R_3$ is a hydrogen atom, a $C_{1-3}$ alkyl or $C_{2-4}$ acyl group;

$R_4$ is a hydrogen atom or $C_{1-5}$ alkyl group;

$R_5$ is a $C_{1-5}$ alkyl group, a straight chain $C_{1-3}$ alkyl group terminally substituted by a chlorine atom; or $R_4$ and $R_5$ are joined so that together with the nitrogen atom to which they are attached they form pyrrolidino or piperidino; and $R_6$ is a $C_{1-5}$ alkyl group;

the $NR_4R_5$ and $OR_3$ moieties are trans; and pharmaceutically acceptable salts thereof.

2. A compound according to claim 1 of the formula (II):

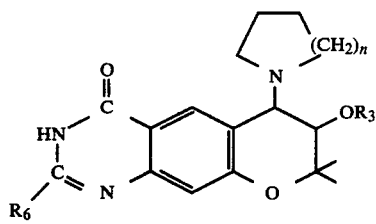

wherein: n is 1 or 2, $R_3$ and $R_6$ are as defined in claim 1 and the cyclic amino and $OR_3$ moieties are trans.

3. A compound according to claim 2 wherein n is 1.

4. A compound according to claim 2, wherein $R_3$ is hydrogen.

5. A compound according to claim 2 or 3, wherein $R_6$ is methyl.

6. Trans-7-hydroxy-6-pyrrolidine-4,6,7,8-tetrahydro-2,8,8-trimethyl-3H-pyrano[3,2-q]quinazolin-4-one.

7. An anti-hypertensive pharmaceutical compositions comprising an anti-hypertensive effective amount of the compound according to claim 1, 2, 3, 4, or 6, and a pharmaceutically acceptable carrier.

8. A method of treatment or prophylaxis of hypertension in mammals, which comprises administering to the sufferer an anti-hypertensive effective amount of the compound according to claim 1, 2, 3, 4, or 6.

* * * * *